United States Patent
Remon et al.

[11] Patent Number: 6,132,769
[45] Date of Patent: Oct. 17, 2000

[54] PHARMACEUTICAL MATRIX PELLETS, TABLETS AND COMPOSITION FOR THE PREPARATION THEREOF

[75] Inventors: Jean-Paul Remon, Ghent; Chris Vervaet, Roeselare, both of Belgium

[73] Assignee: Universiteit Gent, Ghent, Belgium

[21] Appl. No.: 08/619,022

[22] Filed: Mar. 20, 1996

[30] Foreign Application Priority Data

Mar. 21, 1995 [BE] Belgium ............................... 09500248
Mar. 20, 1996 [WO] WIPO ..................... PCT/BE96/00033

[51] Int. Cl.[7] ........................................................ A61K 9/20
[52] U.S. Cl. ......................... 424/464; 424/474; 424/476
[58] Field of Search ................................... 424/464, 474, 424/476

[56] References Cited

U.S. PATENT DOCUMENTS

| | | | |
|---|---|---|---|
| 3,146,167 | 8/1964 | Lantz et al. | 167/82 |
| 4,102,806 | 7/1978 | Kondo et al. | 252/316 |
| 4,235,870 | 11/1980 | Leslie | 424/19 |
| 4,574,080 | 3/1986 | Roswall | 424/20 |
| 4,963,359 | 10/1990 | Haslwanter et al. | 424/440 |

FOREIGN PATENT DOCUMENTS

| | | | |
|---|---|---|---|
| 0 540 460 A1 | 5/1992 | European Pat. Off. | A23L 1/09 |
| 850026111 | 2/1985 | Japan . | |
| 2 081 092 | 2/1982 | United Kingdom | A61K 47/00 |
| 2 204 792 | 5/1987 | United Kingdom | A61K 9/30 |
| 2204792 | 5/1988 | United Kingdom . | |

OTHER PUBLICATIONS

Thomsen, L. et al., "Prolonged Release Matrix Pellets Prepared by Melt Pelletization II. Hydrophobic Substances as Meltable Binders", Drug Development and Industrial Pharmacy, vol. 20 (7), pp. 1179–1197 (1994).
Derwent AN–86–260171 [40] & Japan 61186313 A (Abstract Only).
Derwent AN–90–196838 [26] & Japan 2129120 A (Abstract Only).

*Primary Examiner*—Thurman K. Page
*Assistant Examiner*—D. Faulkner
*Attorney, Agent, or Firm*—Ratner & Prestia

[57] ABSTRACT

The present invention relates to pharmaceutical matrix pellet formulations providing an adequate drug release profile. The matrix of said pellets is formed from:
(a) a hydrophilic compound selected among the group consisting of starch, a starch derivative and mixture thereof, and
(b) a hydrophobic compound selected among the group consisting of wax, micro-crystalline wax and mixture thereof.

12 Claims, 7 Drawing Sheets

PHARMACEUTICAL MATRIX PELLETS, TABLETS AND COMPOSITION FOR THE PREPARATION THEREOF

BACKGROUND OF THE INVENTION

The present invention relates to pharmaceutical matrix pellet formulations providing an adequate drug release profile. The matrix of said pellets is formed from: (a) a hydrophilic compound selected from the group consisting of starch, a starch derivative and a mixture thereof, and (b) a hydrophobic compound selected from the group consisting of wax, microcrystalline wax and a mixture thereof.

It is known to provide pellets with a coating, for example an outer polymer coating, for obtaining a specific drug release profile. The coating of pellets with a polymer layer is time consuming. Furthermore, many parameters (such as the layer thickness, the film quality, film aging, the processing parameters, microdefects in the film, etc . . . ) have an influence on the drug release rate. As the exact control of all these parameters is difficult, pellets have no precise drug release, but have a drug rate varying within a certain range. Furthermore the preparation of the known coated (controlled release) pellets requires several production steps.

So as to try to avoid this drawback, the man skilled in the art would suggest to use a thick polymer layer coating the pellets. The use of thick coating layer is however detrimental as it reduces the release rate.

The aim of the present invention in to solve the problems due to the use of outer polymer coating on pellets. The invention provides matrix pellets not provided with any polymer coating, but having the desired release profile.

SUMMARY OF THE INVENTION

The present invention provides pharmaceutical matrix pellets in which solid particles of pharmaceutically active agent, called drug solid particles in the present specification, are dispersed. In order to adapt the drug release profile, the matrix consists of a mixture of a hydrophobic compound and a hydrophilic compound.

The pharmaceutical matrix pellets of the invention thus comprise:

(a) drug solid particles, (b) a hydrophilic compound selected from the group consisting of starch, a starch derivative and a mixture thereof, and (c) a hydrophobic compound selected among the group consisting of wax, microcrystalline wax and a mixture thereof, in which the hydrophilic compound and the hydrophobic compound are present in amounts and a ratio for ensuring an appropriate drug release.

The hydrophilic compound is preferably a maltodextrine. The desired maltodextrines have preferably a DE (dextrose equivalent) value between 0 and 40, for example a value between 5 and 20.

The hydrophobic compound comprises waxes, and/or microcrystalline waxes which preferably have a melting point between 40° C. and 90° C., most preferably between 50 and 80° C. Very convenient waxes are microcrystalline waxes with a melting point between 58° C. (about 60° C.) and 72° C. (about 70° C.).

The matrix pellets may further contain other additives, for example a compound selected from the group consisting of fatty acids, fats and mixtures thereof.

The matrix pellets of the invention advantageously contain more than 20% by weight of a mixture of the hydrophilic and hydrophobic compounds. Preferably the matrix pellets of the invention contain more than 50%, for example from 60 to 90, or even more, of a mixture of the said hydrophilic and hydrophobic compounds.

According to practical examples of the matrix, the weight ratio of hydrophobic compound selected from the group consisting of wax, microcrystalline wax and a mixture thereof versus hydrophilic compound selected from the group consisting of starch, a starch derivative and a mixture thereof is between 1/10 and 10/1. Advantageously, said ratio is between 3/10 and 10/3, preferably between 1/4 and 2/1. According to specific examples of pellets, the ratio is higher than 0.6, preferably higher than 0.9, most preferably higher than 1, for example above 1.1 (1.14–1.2).

The matrix pellets may contain 10–90% by weight, advantageously more than 15% by weight drug solid particles, preferably more than 25% by weight drug solid particles, most preferably more than 50% by weight drug solid particles.

According to a further embodiment, the weight ratio of drug solid particles versus hydrophobic compound selected among the group consisting of wax, micro-crystalline wax and a mixture thereof is higher than 0.3, advantageously higher than 0.5, preferably higher than 1 (for example between 1 and 5).

Matrix pellets with a weight ratio of hydrophobic/hydrophilic compound above 1 and with a weight ratio of drug solid/hydrophobic compound above 1 allow a slow but nearly constant drug release.

Matrix pellets of the invention have an exceptional stability for their release rate. This is especially the case when the ratio hydrophilic compound/hydrophobic compound is between 10/3 and 3/10, most preferably between 1/2 and 2/1.

The invention also provides an intermediate composition for the preparation of matrix pellets of the invention. The composition comprises: (a) a hydrophilic compound selected from the group consisting of starch, a starch derivative and a mixture thereof, (b) a hydrophobic compound selected from the group consisting of wax, microcrystalline wax and a mixture thereof, and (c) possibly other additives, in which the amount and ratio of (a) and (b) are as described above.

This intermediate composition, is normally used in the form of dry particles, for the preparation of the pharmaceutical matrix pellets.

The intermediate composition has preferably the characteristics mentioned above for the matrix pellets of the invention; i.e. the hydrophilic compound, the hydrophobic compound, and the weight ratio are preferably those mentioned above.

The invention further relates to drug containing dosage forms (such as tablets, pills, suppository, compressed dosage forms) containing matrix pellets of the invention as disclosed above, and to a process for the preparation of matrix pellets of the invention.

The dosage forms of the invention contain a medicinally or pharmaceutically effective amount of drug.

The process for the preparation of matrix pellets containing drug solid particles with an appropriate drug release comprises the following steps:

(a) heating a hydrophobic compound selected from the group consisting of wax, microcrystalline wax and a mixture thereof at a temperature higher than its melting temperature (about the melting temperature or above), (b) mixing together the melted hydrophobic compound, a hydrophilic compound selected from the group consisting of starch, a starch derivative and a mixture thereof, and the drug solid particles, and (c) cooling the mixture hydrophobic compound, hydrophilic compound and drug solid particles to a temperature lower than the melting temperature of said hydrophobic compound so as to obtain matrix pellets with the appropriate drug release.

Advantageously, the process comprises a step of selecting an/or controlling the weight ratio between the said hydrophilic compound and the said hydrophobic compound for ensuring an appropriate drug release.

Preferably, the process comprises a further step of selecting and/or controlling the weight ratio between the solid drug particles and the said hydrophobic compound.

Other characteristics and details of the invention will be apparent from the following description and associated figures.

BRIEF DESCRIPTION OF THE DRAWINGS

FIG. 1 illustrates the use of Waxy Maltodextrine as the hydrophilic compound, 35% (I), 40% (II) or 45% (III) microcrystalline wax with a melting point of ±70° C. as the hydrophobic compound, and 15% ibuprofen as the active compound.

FIG. 2 illustrates the use of Potato Maltodextrine as the hydrophilic compound, 35% (V), 40% (VI) or 45% (VII) microcrystalline wax with a melting point of ±60° C. or 35% (VIII) microcrystalline wax with a melting point of ±70° C., and 15% ibuprofen as the active compound.

FIG. 3 illustrated the use Extruded waxy corn starch as hydrophilic compound, 30% (IX), 35% (X) or 40% (XI) microcrystalline wax with a melting point of ±60° C. as the hydrophobic compound, FIG. 4 illustrates the use Drum dried waxy corn starch as hydrophilic compound, 40% (XII) microcrystalline wax with a melting point of ±70° C., or of 30% (XIV) microcrystalline wax with a melting point of ±70° C. as hydrophobic compound, and 15% ibuprofen.

FIG. 5 illustrates the use Waxy Maltodextrine as hydrophilic compound, microcrystalline wax with a melting point of ±70° C. as hydrophobic compound, and ibuprofen 15% (XV), 25% (XVI), 50% (XVII), 60% (XVIII) and 70% (XIX).

FIG. 6 illustrates the use 50% Extruded waxy corn starch as hydrophilic compound, 35% microcrystalline wax with a melting point of ±60° C. as the hydrophobic compound, and 15% ibuprofen the releases of the drug just after preparation (XX) and 20 months after preparation (XXI) being shown.

FIG. 7 illustrates the use of 50% Potato Maltodextrine as the hydrophilic compound, 35% microcrystalline wax with a melting point of ±60° C., and 15% ibuprofen; the releases of the drug just after preparation (XXII) and 20 months after preparation (XXIII) being shown.

EXAMPLES

Figure 1:
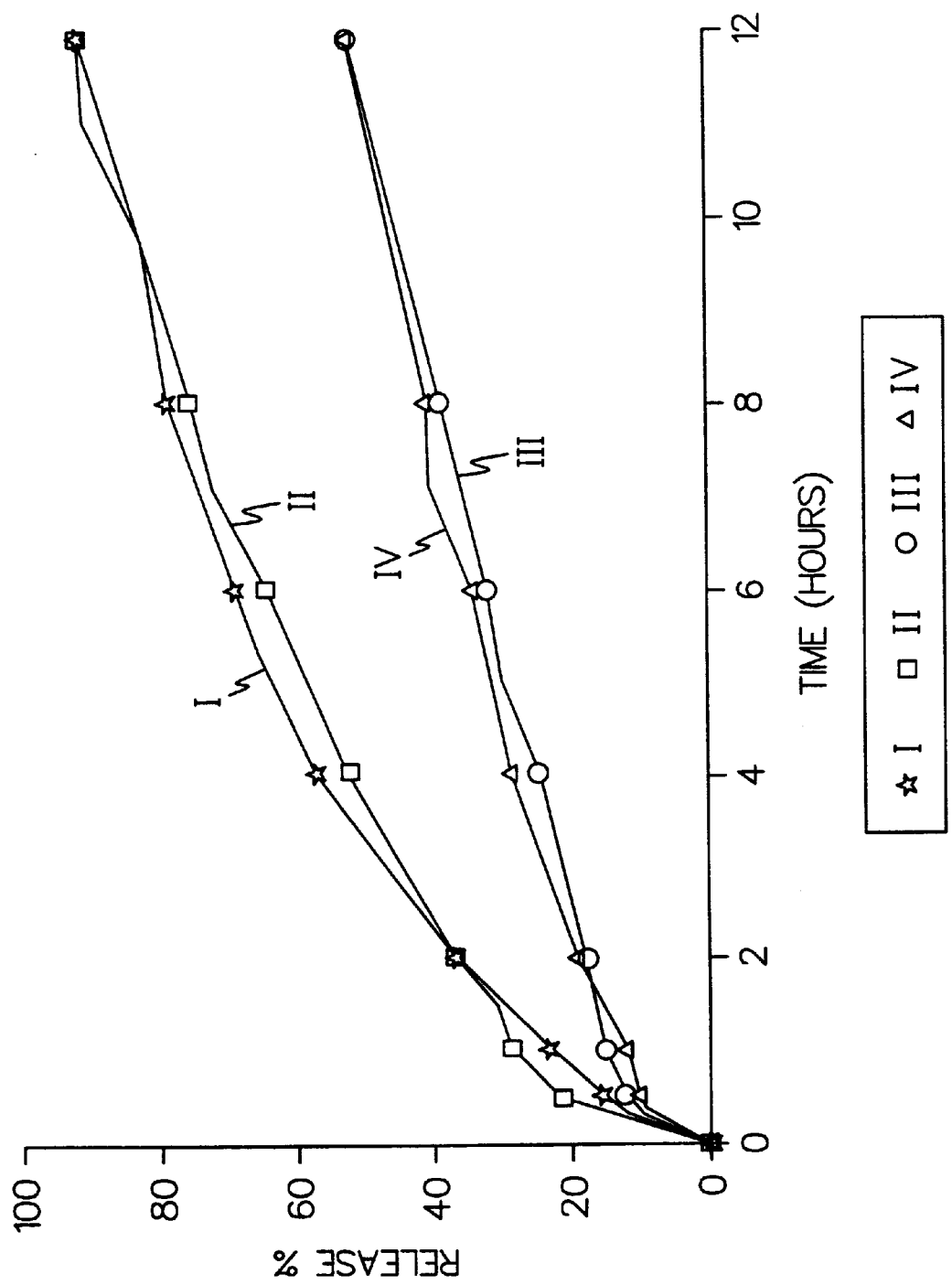
FIGS. 1–7 illustrate the percent release over a period of time of a pharmaceutically active compound from matrix pellets of this invention.
Figure 2:
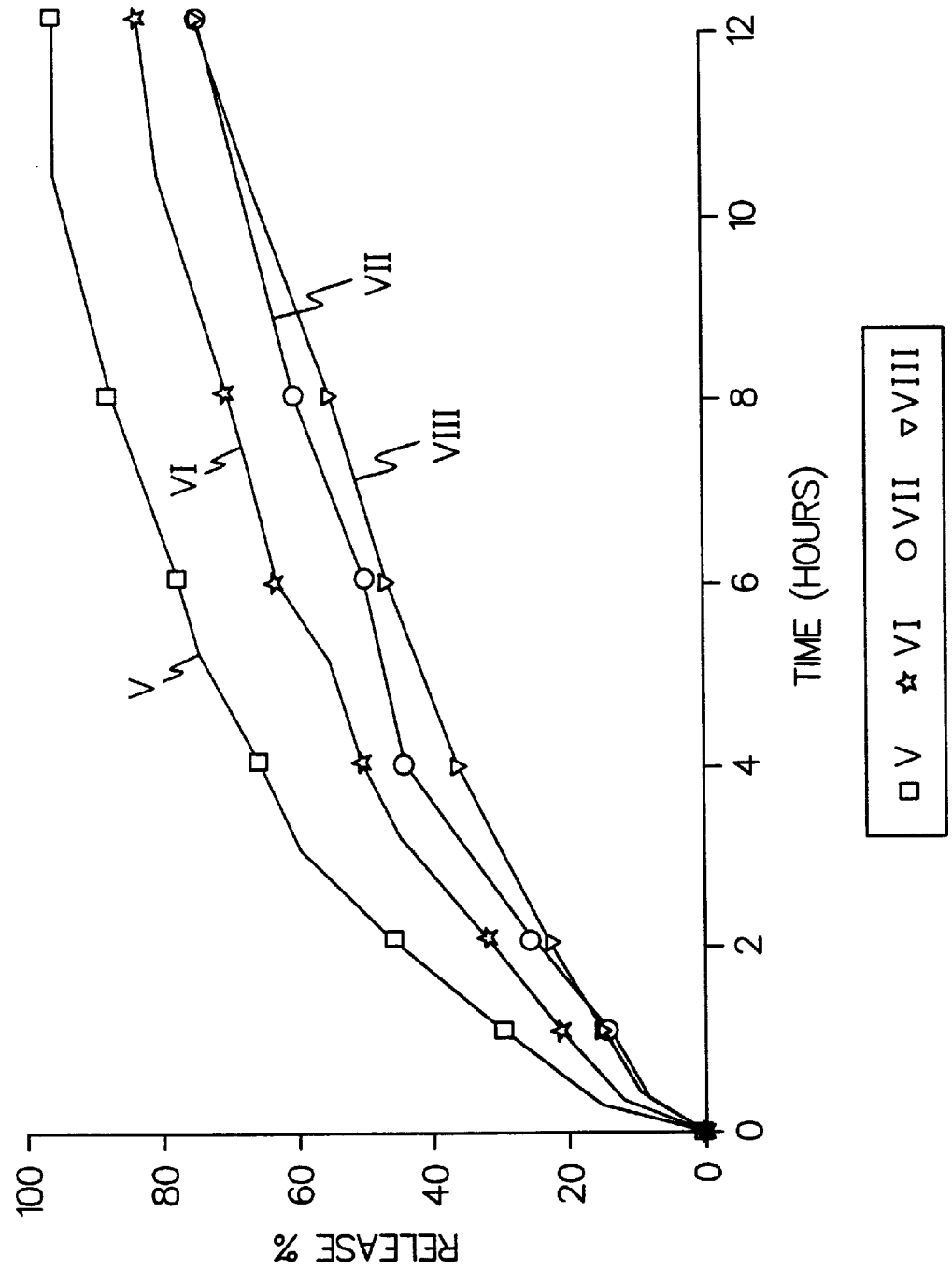
Figure 3:
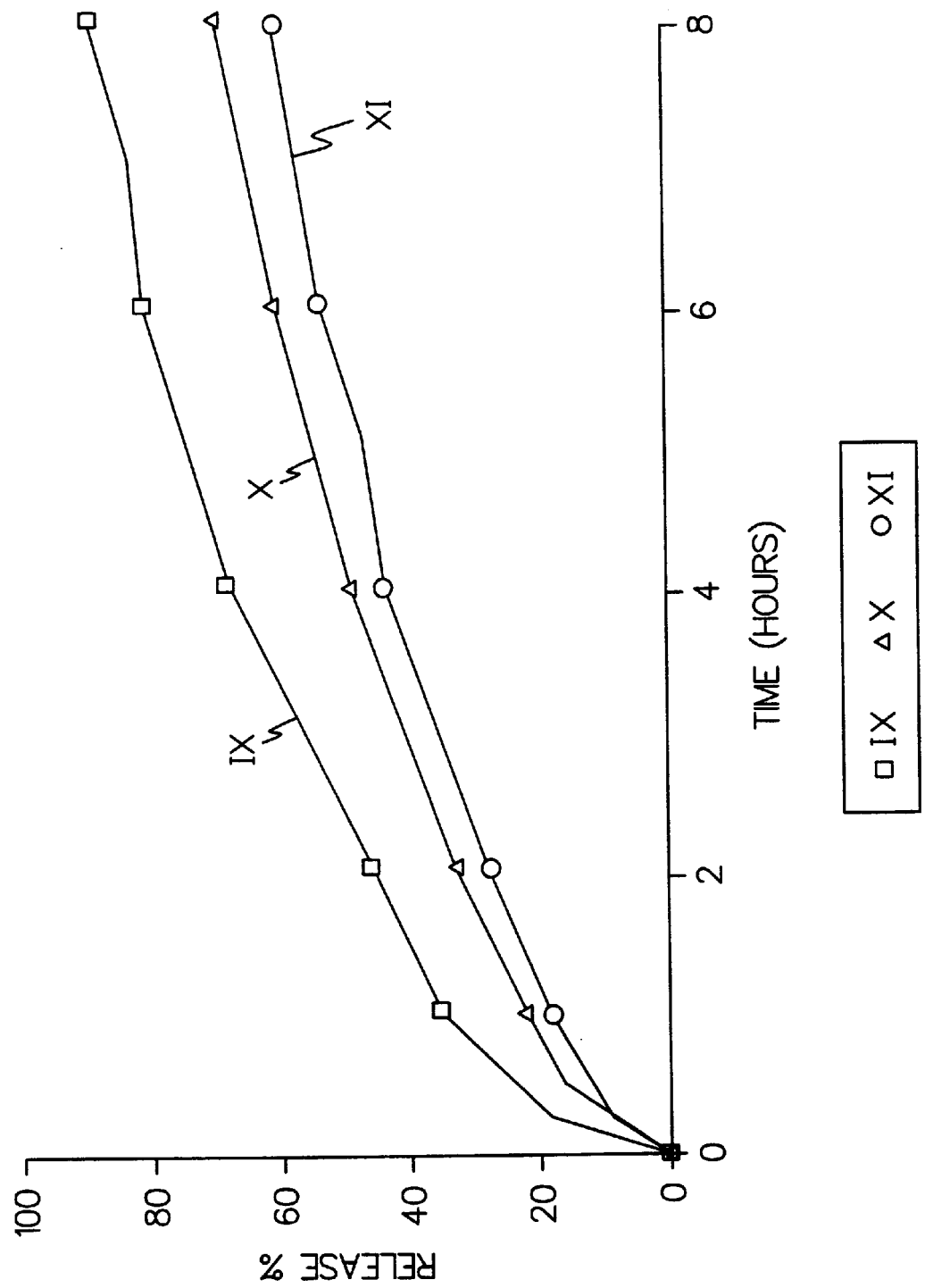
Figure 4:
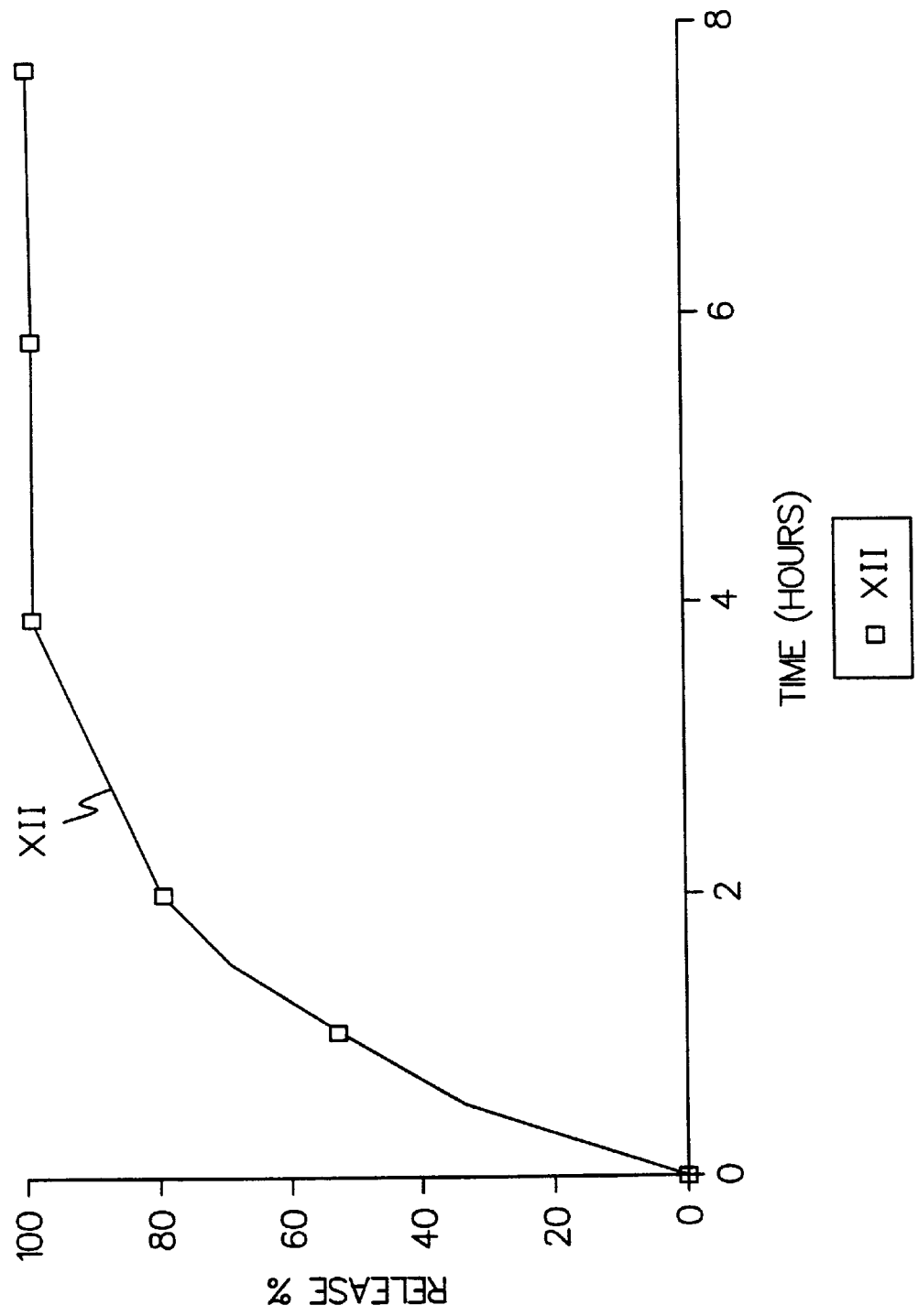

In the examples shown in the table below ibuprofen has been used as the active compound. Ibuprofen had a particle size of ±25 um.

The hydrophobic compounds used were: microcrystalline waxes namely Lunacera® P (Fuller GmbH, Germany) with a melting range between 58–62° C. and Lunacera M® with a melting range between 68–72° C.

As hydrophilic compounds we have used: pregelatinized starches (drum dried corn starch-drum dried waxy corn starch), extruded waxy corn starch and maltodextrines with a DE value (Dextrose Equivalent) of 3 (Potato Maltodextrine) and of 10 (Waxy Maltodextrine).

The matrix was prepared as follows: the wax was melted by heating up to 65° C. in case of the Lunacera P and up to 75° C. for the Lunacera M. Ibuprofen and a starch or a maltodextrine were mixed in a jacketed high shear granulator. During the mixing of ibuprofen and the starch or the maltodextrine, the molten wax was added.

Ibuprofen, wax and starch or maltodextrine were mixed in order to obtain a homogeneous mass. During a slow and controlled cooling of the mass, under continuous stirring, matrix pellets were formed.

The drug release from the matrix pellets was tested using the paddle method (USP XXII at a rotational speed of 100 rpm). During the test, the pellets (amount equivalent with 45 mg ibuprofen) were fixed in a basket and put in a dissolution flask containing 900 mL phosphate buffer (pH 7.2; 37° C.). The ibuprofen release was measured.

In the production method described hereabove, a high shear granulator is used. Other known methods and apparatuses (for example extrusion spheronisation) can be used for the production of matrix pellets.

The following tables give an over view of the matrices produced and tested.

| Composition | Weight % | | | | | | | | | | | | | | | | | | |
| --- | --- | --- | --- | --- | --- | --- | --- | --- | --- | --- | --- | --- | --- | --- | --- | --- | --- | --- | --- |
| | I | II | III | IV | V | VI | VII | VIII | IX | X | XI | XII | XIII | XIV | XV | XVI | XVII | XVIII | XIX |
| Ibuprofen | 15 | 15 | 15 | 15 | 15 | 15 | 15 | 15 | 15 | 15 | 15 | 15 | 15 | 15 | 15 | 25 | 50 | 60 | 70 |
| Lunacera M | | | | 30 | | | | 35 | | | | | | 30 | 30 | 27 | 18 | 18 | 18 |
| Lunacera P | 35 | 40 | 45 | | 35 | 40 | 45 | | 30 | 35 | 40 | 40 | 45 | | | | | | |
| Waxy Maltodextrine (DE = 10) | 50 | 45 | 40 | 55 | | | | | | | | | | | 55 | 48 | 32 | 22 | 12 |
| Patato Maltodextrine (DE = 3) | | | | | 50 | 45 | 40 | 50 | | | | | | | | | | | |
| Starch DDWCS | | | | | | | | | | | | 45 | 40 | 55 | | | | | |
| Starch EWCS | | | | | | | | | 55 | 50 | 45 | | | | | | | | |

-continued

| Composition | Weight % | | | | | | | | | | | | | | | | | | |
|---|---|---|---|---|---|---|---|---|---|---|---|---|---|---|---|---|---|---|---|
| | I | II | III | IV | V | VI | VII | VIII | IX | X | XI | XII | XIII | XIV | XV | XVI | XVII | XVIII | XIX |
| Weight ratio wax/starch or maltodextrine | 0,7 | 0,9 | 1,1 | 0,6 | 0,7 | 0,9 | 1,1 | 0,7 | 0,6 | 0,7 | 0,9 | 0,9 | 1,1 | 0,6 | 0,55 | 0,55 | 0,55 | 0,02 | 1,5 |
| Weight ratio drug/wax | 0,4 | 0,4 | 0,3 | 0,5 | 0,4 | 0,4 | 0,3 | 0,4 | 0,5 | 0,4 | 0,4 | 0,4 | 0,3 | 0,5 | 0,5 | 1 | 2,8 | 3,3 | 3,8 |

The figures indicate that by modifying the wax content (see for example composition II and III), the release from the matrixes can be adjusted. The release depends also on the type of wax used (see for example composition V and VII). When examining the release profiles of compositions II, III, V, VI, VII, IX, X, XI, it appears that when increasing the ratio wax/starch the release rate is reduced.

Figure 5:
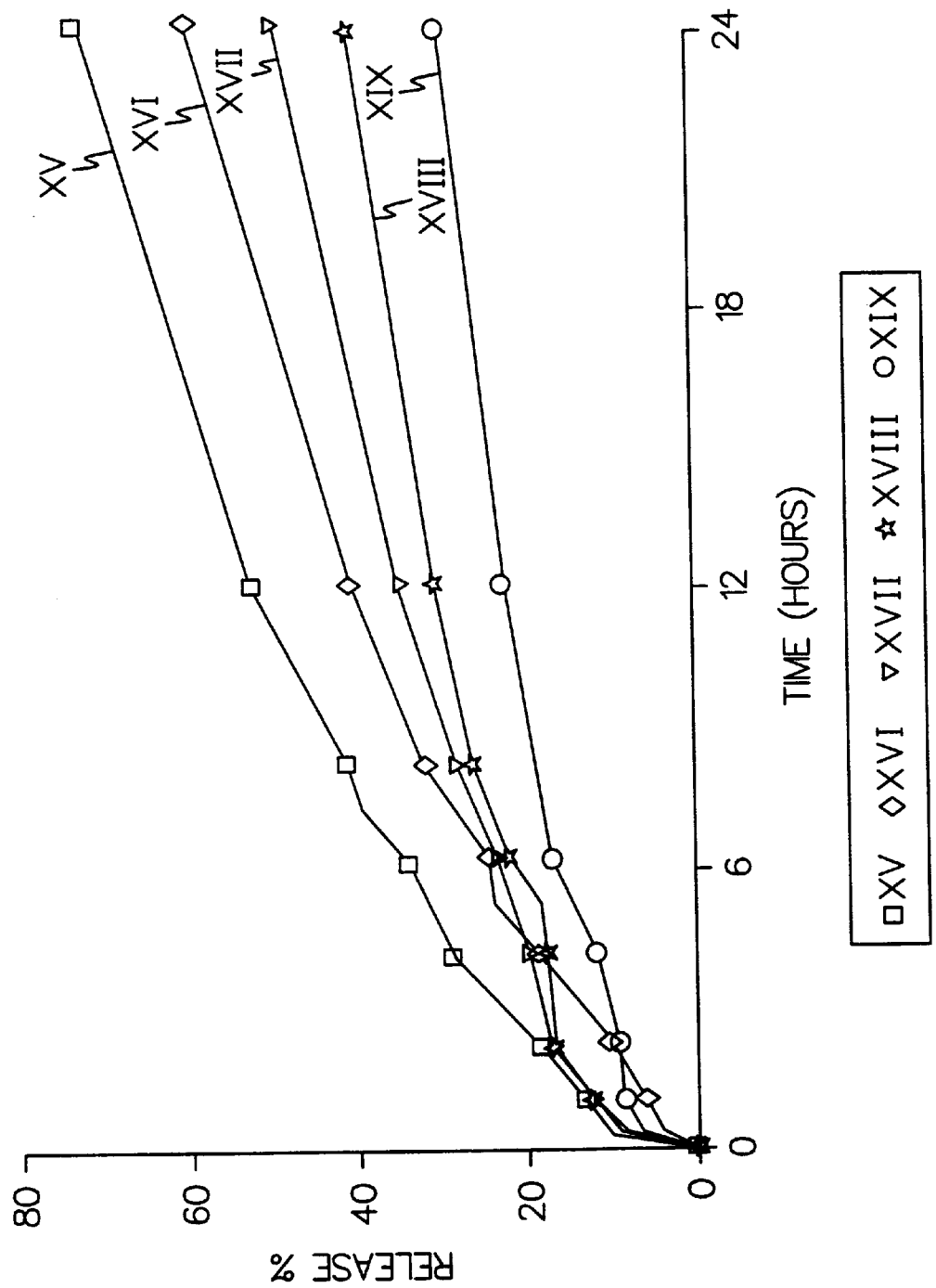

FIG. 5 shows that the matrix effect remains for pellets with a high drug loading. When examining the release profiles of the compositions XV, XVI and XVII, it appears that for a ratio wax/maltodextrine, the release rate will decrease with the drug content. Indeed, after 24 hours, about 75% of the 15% of ibuprofen is released (i.e. 0.75×15= 11.25%) for the composition XV; after 24 hours, about 57% of the 25% of ibuprofen is released (i.e. 0.57×25=14.25%) for the composition XVI, and after 24 hours, about 45% of the 50% of ibuprofen is released (i.e. 0.45×50=22%) for the composition XV. It means that the presence of a higher drug content in some pellets will not greatly affect the release rate required. It means thus also that a different drug content in the pellets will not have a major influence on the drug release. Indeed, a difference of 10% of the drug content in the pellets (i.e. a drug content of 11% instead of 10%) will only increase the drug release after 24 hours of less than 1% (about less than 0.5%), when having always the same ratio wax/maltodextrine or starch.

The figures show that the pellets III having a weight ratio wax/starch or maltodextrine of 1.1 and pellets XIX with a weight ratio of 1.5 have a slow and nearly constant ibuprofen release.

Such a slow and nearly constant drug release is also obtained for pellets XVI up to XIX with a weight ratio drug/wax above 1. Pellets having a nearly constant release rate can thus simply be produced by ensuring that the ratio drug/wax is above 1.

The figures show also that when using a specific wax and a specific starch or maltodextrine, and when having a specific drug content in the pellets, an increase of the wax content will lead to a diminution of the release rate.

Figure 6:
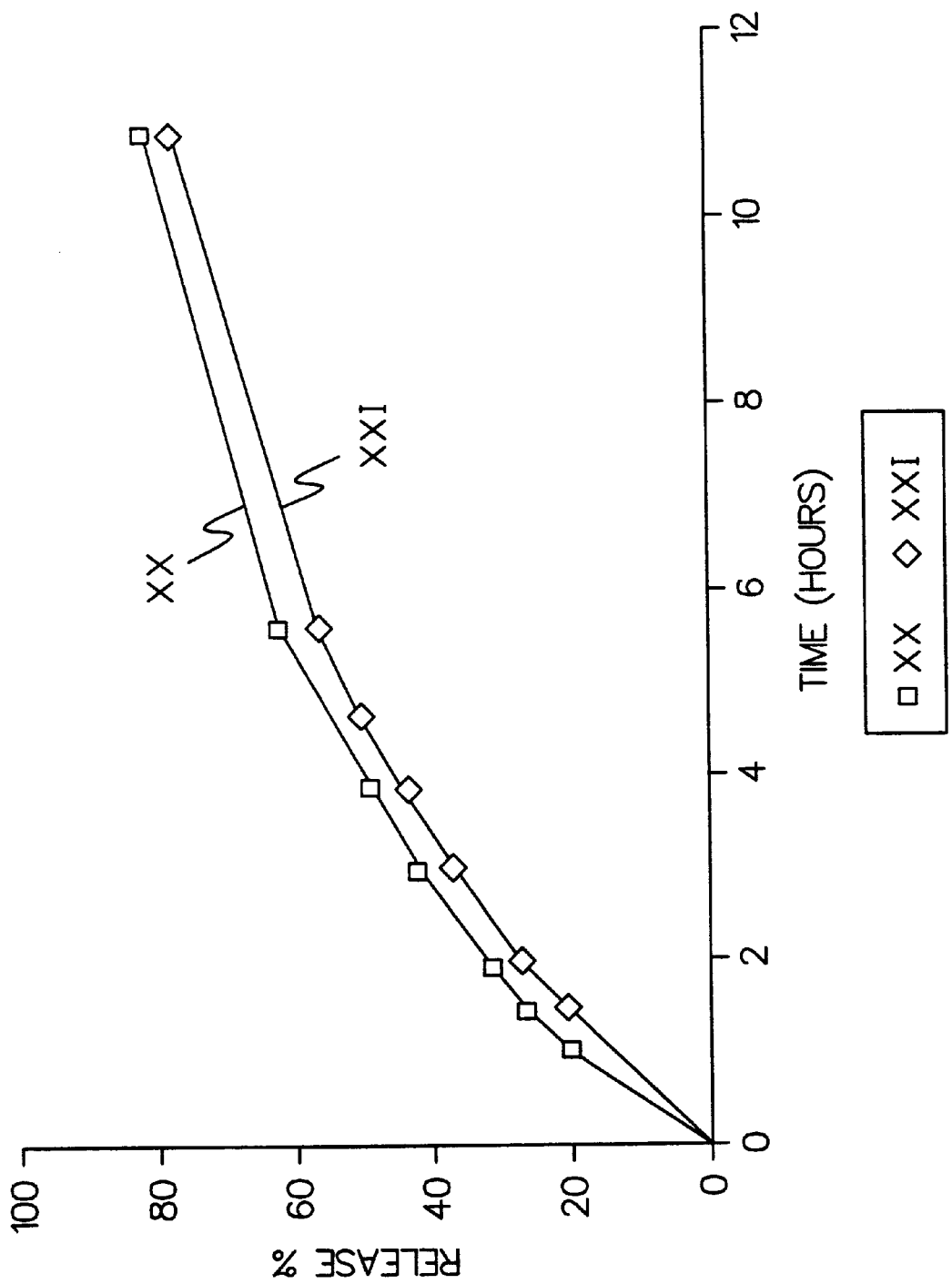
Figure 7:
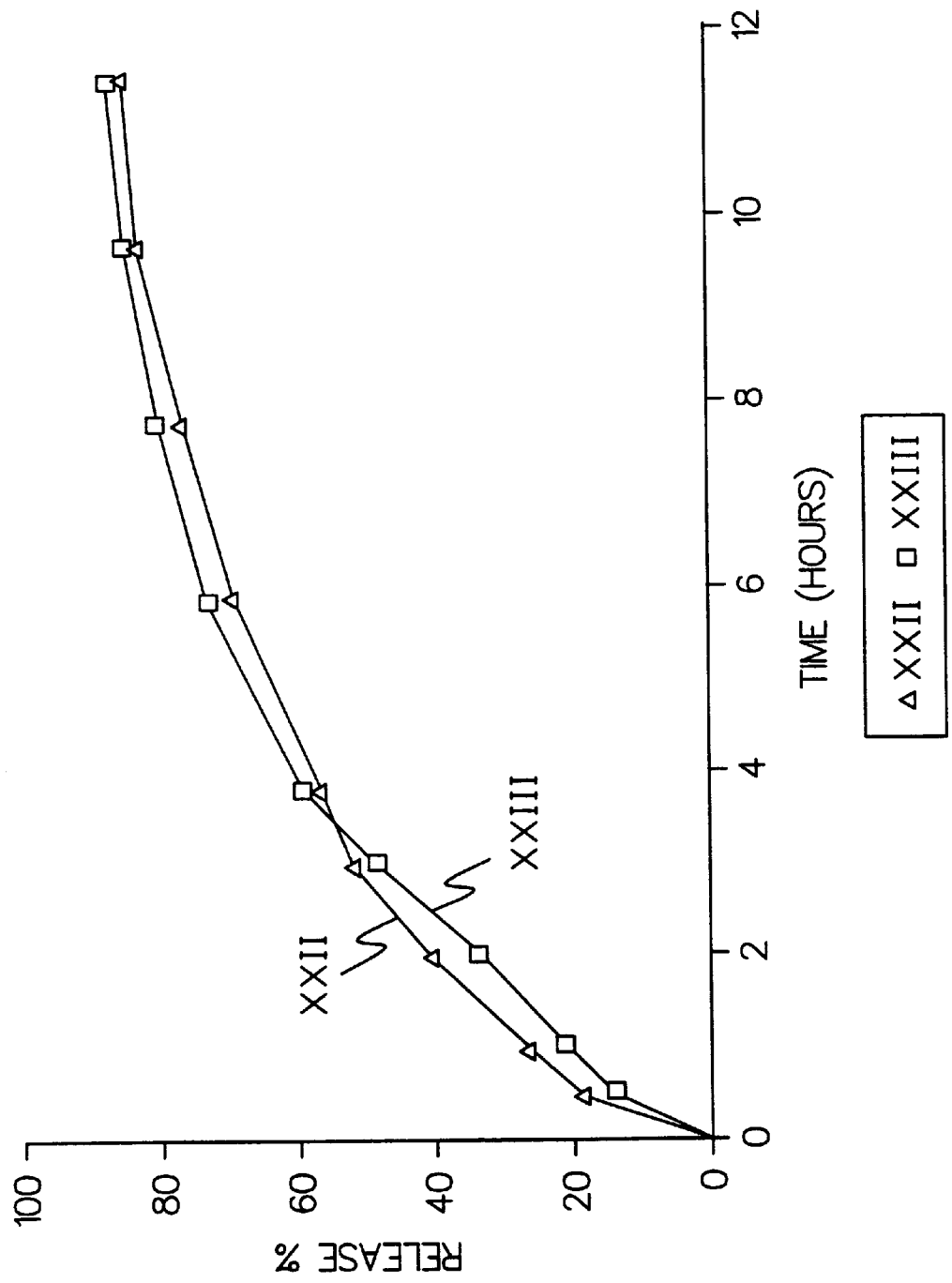

FIGS. 6 and 7 show that the pellets of the invention have an exceptional stability. Indeed the difference between the release rate after 12 hours of pellets just prepared, and the release rate after 24 hours of pellets prepared 20 months ago is less than about 1%. This is a further major advantage of matrix pellets of the invention with respect to pellets provided with a coating for the control of the release rate.

The matrix pellets which can contain up to 80% or even 90% drug (ibuprofen particles in the examples disclosed hereabove) can contain as drugs:
  antipyretic drugs;
  analgesics;
  anti-anginosa (Verapamil, Nifidipine, Dilthiazem, . . . );
  antarrhytmics (disopyramide, quinidine, . . . );
  antihypertensive drugs (B-blocking agents, clonidine, ACE inhibitors, etc . . . );
  diuretics;
  antihypotensive drugs;
  drugs used in the treatment of cerebral vascular diseases (isoxsuprine, . . . );
  narcotic drugs;
  neuroleptics;
  anti-depressive drugs;
  anti-epileptics;
  hormones;
  drugs used in the treatment of bronchospasm (theophylline, . . . );
  drugs used in the treatment of rhinitis and sinusitis;
  ibuprofen, and
  mixtures thereof.

The matrix pellets of the invention can be used for the preparation of tablets. For example, tablets can be prepared by compression of the matrix pellets of the examples I to XIX.

We claim:

1. Pharmaceutical matrix pellets comprising from 10% to 90% by weight of drug solid particles dispersed throughout a controlled release matrix, said matrix consisting essentially of (a) a hydrophilic compound selected from the group consisting of starch, a starch derivative having a DE value between 3 and 20, or a mixture thereof and (b) a hydrophobic compound selected from the group consisting of wax, microcrystalline wax and a mixture thereof, said hydrophilic and hydrophobic compounds being present in amounts and in a ratio providing a selected drug release rate, the weight ratio of hydrophobic compound to hydrophilic compound being between 1/10 and 10/1.

2. A tableted drug dosage form comprising a medicinally effective amount of drug solid particles dispersed throughout a controlled release matrix, said matrix consisting essentially of (a) a hydrophilic compound selected from the group consisting of starch, a starch derivative having a DE value between 3 and 20 or a mixture thereof and (b) a hydrophobic compound selected from the group consisting of wax, microcrystalline wax and a mixture thereof, said hydrophilic and hydrophobic compounds being present in amounts and in a ratio providing a selected drug release rate, the weight ratio of hydrophobic compound to hydrophilic compound being between 1/10 and 10/1.

3. The matrix pellets of claim 1 in which the weight ratio of hydrophobic compound to hydrophilic compound is between 3/10 and 10/3.

4. The matrix pellets of claim 1 in which the weight ratio of hydrophobic compound to hydrophilic compound is between 1/2 and 2/1.

5. The matrix pellets of any of claims 1, 3, or 4 in which the weight ratio of drug to hydrophobic compound is in the range of from 0.3/1 to 5/1.

6. The matrix pellets of claim 5 in which the hydrophilic compound is a maltodextrine.

7. The tableted dosage form of claim 2 in which the weight ratio of hydrophobic compound hydrophilic compound is as set forth in claim 3, or 4.

8. The tableted dosage form of claim 7 in which the weight ratio of drug to hydrophobic compound is in the range of 0.3/1 to 5/1.

9. The tableted dosage form of claim 7 in which the hydrophilic compound is maltodextrine.

10. A process for preparation of controlled release matrix pellets comprising
   (a) heating a hydrophobic compound selected from the group consisting of wax, microcrystalline wax and a mixture thereof at a temperature above the melting point of the hydrophobic compound,
   (b) mixing the melted hydrophobic compound with a hydrophilic compound selected from the group consisting of starch, a starch derivative having a DE value between 3 and 20, and a mixture thereof and drug solid particles, at a weight ratio of hydrophobic compound to hydrophilic compound between 1/10 and 10/1,
   (c) cooling the resulting mixture to a temperature below the melting temperature of the hydrophobic compound, and
   (d) forming drug matrix pellets having a selected drug release rate.

11. The process of claim 10 including the additional step of selecting the weight ratio beteen the hydrophobic compound and the hydrophilic compound to provide the desired drug release rate.

12. The process of claim 11 including the additional step of selecting the weight ratio between the solid drug particles and the said hydrophobic compound to provide the the selected drug release rate.

* * * * *